(12) United States Patent
Sembritzki

(10) Patent No.: US 6,850,594 B2
(45) Date of Patent: Feb. 1, 2005

(54) METHOD FOR MEASURING THE DOSE DISTRIBUTION IN A COMPUTED TOMOGRAPHY APPARATUS

(75) Inventor: Otto Sembritzki, Wachenroth (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/443,638

(22) Filed: May 22, 2003

(65) Prior Publication Data
US 2004/0005029 A1 Jan. 8, 2004

(51) Int. Cl.⁷ .................................................. H05G 1/44
(52) U.S. Cl. .............................. 378/108; 378/4; 378/19
(58) Field of Search ............................ 378/108, 4, 19, 378/146

(56) References Cited

U.S. PATENT DOCUMENTS

| | | | | |
|---|---|---|---|---|
| 4,398,302 A | * | 8/1983 | Pfeiler | 378/146 |
| 5,164,977 A | * | 11/1992 | Vlasbloem et al. | 378/146 |
| 5,210,782 A | * | 5/1993 | Geluk et al. | 378/146 |
| 5,305,367 A | * | 4/1994 | Mulder | 378/146 |
| 6,134,292 A | | 10/2000 | Hsieh | |

* cited by examiner

Primary Examiner—David V. Bruce
Assistant Examiner—Irakli Kiknadze
(74) Attorney, Agent, or Firm—Schiff Hardin LLP

(57) ABSTRACT

In a method for measuring the dose distribution in a computed tomography apparatus, wherein the dose distribution of an X-ray beam emitted by an X-ray tube with a thickness prescribed by a radiation diaphragm is acquired in the thickness direction for at least one setting of the radiation diaphragm, the dose distribution is acquired in the thickness direction with detector elements of a detector line of the computed tomography system in front of which a slit diaphragm is attached, while adjusting the radiation diaphragm so that each possible setting is set. The dose distribution can be acquired in automated fashion and without manual evaluation that is susceptible to error.

17 Claims, 3 Drawing Sheets

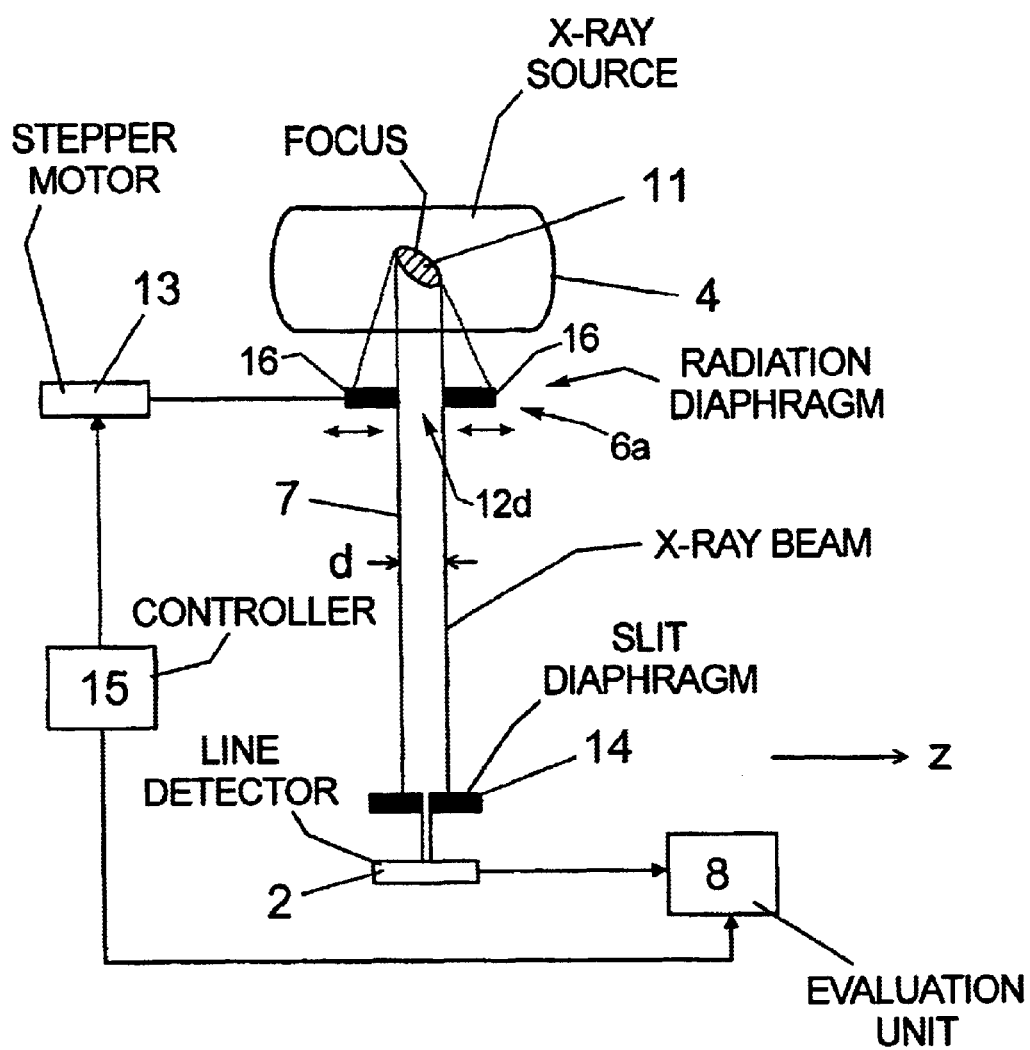

ured the dose distribution in a computed tomography apparatus, wherein the dose distribution of an X-ray beam emitted by an X-ray tube with a thickness prescribed by a radiation diaphragm is acquired in the thickness direction for at least one setting of the radiation diaphragm.

METHOD FOR MEASURING THE DOSE DISTRIBUTION IN A COMPUTED TOMOGRAPHY APPARATUS

BACKGROUND OF THE INVENTION

1. Field of the Invention

The present invention is directed to a method for measuring the dose distribution in a computed tomography apparatus, wherein the dose distribution of an X-ray beam emitted by an X-ray tube with a thickness prescribed by a radiation diaphragm is acquired in the thickness direction for at least one setting of the radiation diaphragm.

2. Description of the Prior Art

A computed tomography apparatus has, among other things, an X-ray tube, an X-ray detector with one or more lines and a patient table. The X-ray tube and the X-ray detectors are arranged at a gantry that rotates around the patient table or an examination axis that proceeds parallel thereto. As an alternative, the X-ray detectors can be arranged around the patient table on a stationary detector ring, with only the X-ray tube moving with the gantry.

The patient table is usually displaceable along the examination axis relative to the gantry. The X-ray tube generates a ray bundle that is spread fan-shaped in a slice plane perpendicular to the examination axis. This limitation of this ray bundle in the direction of the slice thickness is set by the size or diameter of the focus on the target material of the X-ray tube and by one or more radiation diaphragms arranged in the beam path of the X-ray bundle. These radiation diaphragms can have an adjustable aperture width for generating different thicknesses of the X-ray bundle. Further, radiation diaphragms having diaphragm apertures of different widths arranged next to one another are known that can be shifted to different positions in the slice thickness direction by means of a stepping motor, in order to set different thicknesses of the X-ray bundle. During an examination, the X-ray bundle penetrates a slice of a subject, for example a body slice of a patient, placed on the patient table, and strikes the X-ray detectors lying opposite the X-ray tube. The angle at which the X-ray bundle penetrates the body slice of the patient, and possibly the position of the patient table relative to the gantry, change continuously during the image acquisition with the computed tomography apparatus.

The intensity of the X-rays of the X-ray beam that strike the X-ray detectors after penetrating the patient is dependent on the attenuation of the X-rays by the patient. Dependent on the intensity of the received X-rays, each of the X-ray detectors generates a voltage signal that corresponds to a measurement of the overall transparency of the body for X-rays proceeding from the X-ray tube to the corresponding X-ray detector. A set of voltage signals of the X-ray detectors that correspond to attenuation data acquired for a specific position of the X-ray source relative to the patient is referred to as a projection. A set of projections that were acquired at different positions of the gantry during the revolution of the gantry around the patient is referred to as a scan. The computed tomography apparatus acquires many projections at different positions of the X-ray source relative to the body of the patient in order to reconstruct an image that corresponds to a two-dimensional tomogram of the body of the patient or to a three-dimensional image. The standard method for the reconstruction of a tomogram from acquired attenuation data is known as the method of filtered back-projection.

Typical slice thicknesses that are acquired with a computed tomography apparatus in a projection or during a scan lie in the range between 1 and 10 mm. The desired slice thicknesses can be set by the radiation diaphragm at the tube side. An important quality feature of a computed tomography apparatus is thereby the precision with which the thickness of the X-ray bundle that has been set and that corresponds to the slice thickness, is in fact achieved. Conventionally, a portion of an X-ray film in the beam path of the X-ray bundle for each collimation or slice thickness achievable by adjustment of the radiation diaphragm has been irradiated for quality assurance, particularly before the delivery of a computed tomography apparatus or after maintenance or repair work. The film is successively displaced by a defined distance and then irradiated with the next collimation. After developing the film, the width of the blackening generated with the X-ray bundle is measured as a criterion for the dose width. The precision with which the thickness of the X-ray bundle that has been set is in fact achieved can be recognized on the basis of this measured width.

This conventional procedure for quality assurance, however, is complicated and requires manual, and thus error-prone, evaluation of the film.

U.S. Pat. No. 6,134,292 discloses a method and an apparatus for the correction of image data with regard to an inhomogeneous distribution of the X-rays as well as with regard to the detector sensitivity of a computed tomography apparatus in the z-direction. In this method, the dose distribution of an X-ray bundle emitted by the X-ray tube having a thickness prescribed by a radiation diaphragm is acquired in the thickness direction by a setting of the radiation diaphragm in order to obtain a dose profile in the z-direction, on the basis of which the image data can be corrected. The publication, however, is not concerned with the aforementioned problem.

SUMMARY OF THE INVENTION

An object of the present invention is to provide a method for measuring the dose distribution in a computed tomography apparatus that requires less outlay and is less susceptible to error than conventional techniques.

This object is achieved in accordance with the invention in a method wherein the dose distribution of the X-ray bundle that is emitted by the X-ray tube and, in particular, that is spread fan-shaped and has a thickness prescribed by a radiation diaphragm or by a radiation diaphragm system is not acquired in the thickness direction by means of a film for at least one setting of the radiation diaphragm, but instead is acquired with the detector elements of the detector line of the computed tomography apparatus. To this end, a slit diaphragm that is narrow in the slice thickness direction is attached in front of the detector elements, and the radiation diaphragm is displaced in the slice thickness direction either continuously or in steps. A topogram of the dose distribution of the X-ray bundle in the slice thickness direction is recorded by means of this displacement of the radiation diaphragm of the tube side from a position wherein no X-rays are incident on the detector elements through the slit diaphragm arranged at the detector side, across the position at which the maximum of the X-ray intensity is incident on the detector elements, and up to a position at which again no X-rays proceed through the slit diaphragm to the detector elements.

The half-intensity width of the dose distribution for the selected setting of the radiation diaphragm can be automatically determined in computerized fashion from this topogram. Further, the inventive method not only supplies this width but also the exact distribution of the X-ray dose over the slice thickness. For example, the point along the width of the dose distribution at which the dose has dropped to 1/10 of the maximum value also can be determined in this way. Further, the steepness of the lateral edges of the dose distribution can be calculated, this likewise representing a criterion for the quality of the computed tomography apparatus.

The present invention thus offers a simple possibility for measuring the dose distribution of a computed tomography apparatus that no longer requires film exposure or any additional manual activity during the measurement. An X-ray film need not be developed, so that the evaluation event, which can be automatically implemented computer-supported, is concluded faster. A manual and thus error-prone evaluation of the blackening of a film is no longer required. The dose width is no longer merely determined as a numerical value; rather, the entire curve of the dose profile is available and can be made available to other components and can be graphically presented.

The displacement of the radiation diaphragm in front of the X-ray tube during the measurement preferably ensues automatically with an appropriate drive. Upon implementation of the method with a computed tomography apparatus that has a radiation diaphragm with diaphragm apertures of different widths lying side-by-side, the stepping motor that is already present therein can be utilized for the displacement of the radiation diaphragm, from which the current position of the radiation diaphragm also can be acquired. Of course, the current position of the radiation diaphragm alternatively can be acquired with some other position recognition.

There is also the possibility of utilizing a radiation diaphragm at the tube side that has two elements that are displaceable or movable relative to one another. Broad and narrow diaphragm apertures thus can be generated by moving these displaceable elements more or less close together. Using this manner of producing diaphragm apertures, the measurement can ensue such that the spacing of the two displaceable elements is retained but their position is displaced in the same way. This is preferably successively implemented for all provided spacings or diaphragm apertures.

In one embodiment of the present invention, the radiation diaphragm is displaced with constant speed during the measurement, so that the dose width can be determined from the measured dose profile taking this speed into consideration. In a further embodiment the radiation diaphragm can be displaced in steps, with a measurement of the dose being undertaken after every displacement step. The exact width of the dose distribution then can be likewise determined from the knowledge of the respective measurement positions of the radiation diaphragm.

In the implementation of the present method, the dose distribution preferably is measured not just for one setting of the radiation diaphragm, but at all available settings in succession. Given the use of a radiation diaphragm having diaphragm apertures lying side-by-side, this can be realized very simply by means of a complete displacement of the radiation diaphragm over the entire available diaphragm range, i.e. through all diaphragm apertures.

The slit diaphragm utilized in front of the X-ray detectors preferably has a width of the diaphragm aperture of <1 mm in the slice thickness direction. This slit diaphragm can be attached to a mount of the patient table, so that no additional measures are required for attaching the slit diaphragm to the computed tomography apparatus.

DESCRIPTION OF THE DRAWINGS

FIG. 4 shows the illustration of FIG. 2 with an alternative version of the radiation diaphragm.

DESCRIPTION OF THE PREFERRED EMBODIMENTS

Figure 1:
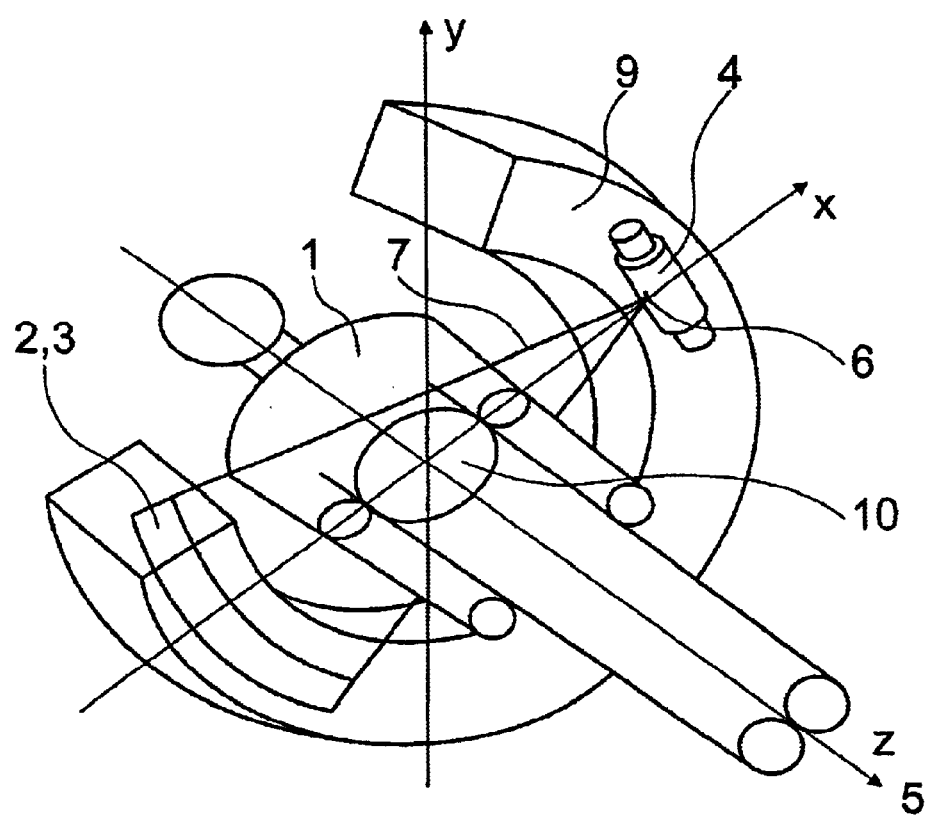
FIG. 1 is a schematic view of a part of a computed tomography apparatus for acquiring tomograms of a body slice of a patient.

In a schematic view, FIG. 1 shows a part of a computed tomography system for illustrating the geometrical relationships in the acquisition of measured data. The computed tomography system has an X-ray source in the form of an X-ray tube 4 that emits a fan-shaped X-ray bundle 7 in the direction of a detector bank having a line 2 composed of detector elements 3 (only a few of which are shown in FIG. 1). The X-ray tube 4 as well as the detector elements 3 are arranged at a gantry 9 that can rotate continuously around a patient 1. The patient 1 lies on a patient table (not shown in FIG. 1) that extends into the gantry 9. The gantry 9 rotates in the x-y-plane of a Cartesian coordinate system x-y-z indicated in FIG. 1. The patient table is movable along the z-axis, which corresponds to the slice thickness direction 5 of slices of the patient 1 to be acquired and displayed. FIG. 1 also shows the slice 10 transirradiated by the X-ray bundle 7 for which a tomogram is to be produced.

The expanse of the X-ray beam 7 in the slice thickness direction 5 (z-direction) is prescribed in the present example by the aperture of a radiation diaphragm 6 in front of the X-ray tube 4. This expanse, which ideally leads to a parallel X-ray bundle 7 having a corresponding thickness, cannot be seen from FIG. 1.

Figure 2:
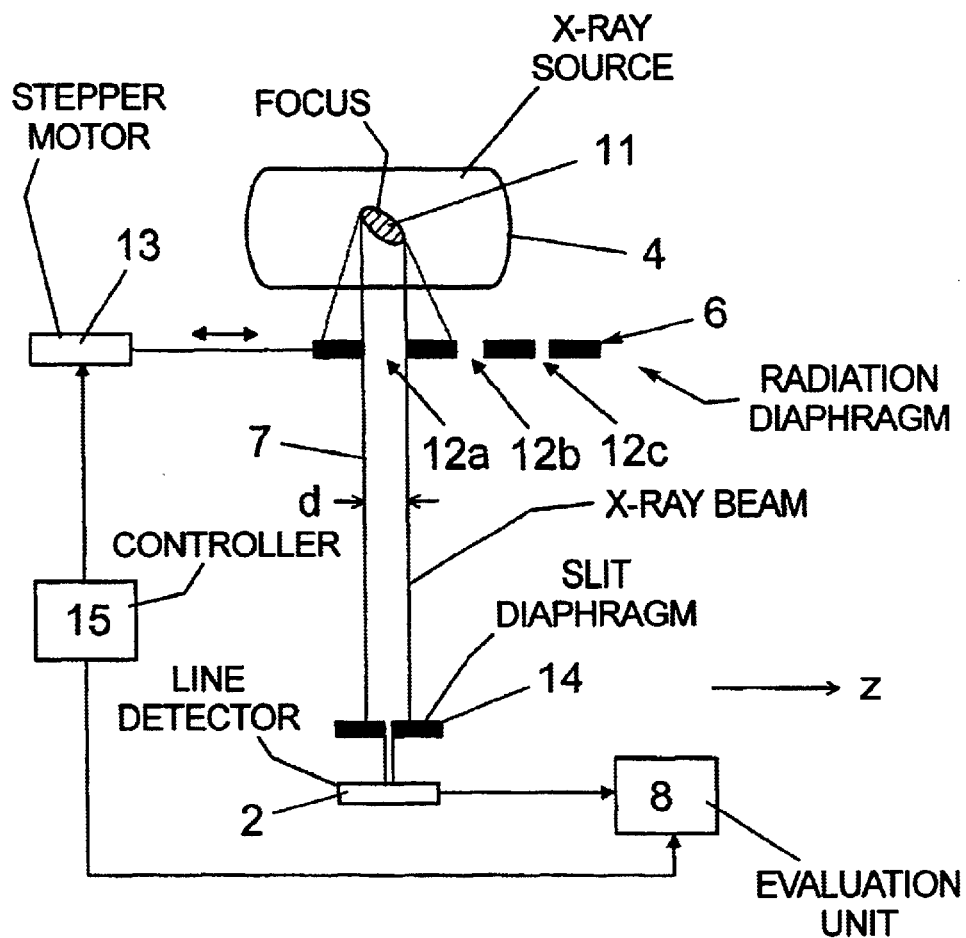
FIG. 2 is a simplified illustration of the limitation of the fan-shaped X-ray bundle by a radiation diaphragm at the tube side as well as the slit diaphragm arranged at the detector side for implementing the inventive method.

In a highly schematic fashion, FIG. 2 again shows the beam relationships in a computed tomography system in a section perpendicular to the slice direction 5. FIG. 2 shows the X-ray tube 4 with the diaphragm system 6 arranged in front of it as well as the detector line 2 that is arranged thereto. An X-ray bundle 7 having the thickness d that is spread fan-shaped is emitted from the focus 11 of the X-ray tube, the thickness d being prescribed by the diaphragm aperture 12a of the diaphragm system 6 at the tube side. In the present example, a diaphragm system 6 is employed having a number of side-by-side diaphragm apertures 12a, 12b, 12c of different aperture widths. By displacing this diaphragm system 6 with a stepper motor 13 in the direction indicated with the double arrow, different thicknesses d of the X-ray beam 7, by which the slice thickness of the transirradiated body slice is defined, can be generated.

As an alternative, FIG. 4 shows a further radiation diaphragm 6a that can be employed, this being composed of two displaceable plates or leaves 16 that limit the diaphragm aperture 12 and by which different widths of the diaphragm aperture 12d can be set also by the stepper motor 13. The displacement possibilities of the displaceable elements 16 are indicated with double arrows.

In the exemplary embodiments, the displacement mechanism with the stepper motor 13 that is already present is utilized for the implementation of the method for measuring the dose distribution. For this measurement, a mechanical auxiliary diaphragm 14 is attached in the beam path over (in front of) the detector line 2. This is a slit diaphragm that is narrow in the z-direction and has a diaphragm aperture with a width of <1 mm in the z-direction. In the exemplary embodiments, this slit diaphragm 14 is secured directly to the patient table (not shown).

Figure 3:
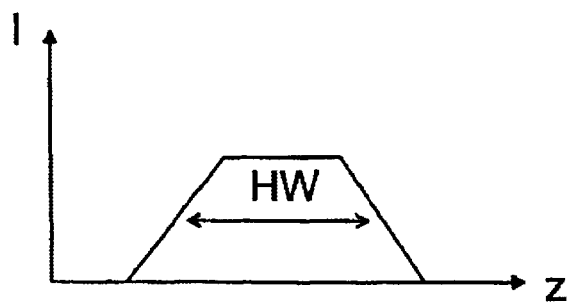
FIG. 3 is an example of the dose distribution measured with the inventive method for a setting of the radiation diaphragm.

The measurement begins with the radiation diaphragm 6 in a position at which the connecting line between the focus 11 and the aperture of the slit diaphragm 14 is interrupted by the left edge of the radiation diaphragm 6 in the exemplary embodiments, so that no X-ray reach the detector 3. The measurement begins at this start position, the measurement being implemented, due to the fastening of the slit diaphragm 14 to the patient table, without advancing the table and without rotation of the gantry 9. During the measurement, the diaphragm 6 at the tube side is continuously displaced through all diaphragm apertures 12a, 12b and 12c with the stepper motor 13 in the embodiment of FIG. 2, or the plates 16 are adjusted through all possible positions in the embodiment of FIG. 4. As a result, all slice thicknesses that can be set with the radiation diaphragm 6 or 6a are successively traversed. The readings thereby measured with the detector elements 3 are acquired as a topogram and preferably are presented at a monitor. The half intensity width can be evaluated from the dose distribution measured as a result, this being shown as an example in FIG. 3 on the basis of the measurement of a single diaphragm setting, or set slice thickness.

The displacement of the radiation diaphragm 6 or 6a with the stepper motor 13 as well as the computer-supported evaluation of the dose profile ensue automated in the exemplary embodiments, with a controller 15 for the displacement of the radiation diaphragm 6 or 6a and an evaluation unit 8 for the determination of the dose width from the measured dose profile being provided. The evaluation unit 8 receives the information about the speed with which the radiation diaphragm 6 or 6a was displaced during the measurement or about the actual position of the diaphragm 6 or 6a present at various measuring times from the controller 15.

The method according to the exemplary embodiments can be realized in a simple way in known computed tomography systems by integrating appropriate auxiliary modules in the software for the displacement of the radiation diaphragm 6 or 6a with the already-existing stepper motor 13 and the appertaining mechanisms, as well as for the evaluation function of the tomogram data that are measured. The user merely has to attach the slotted diaphragm 14 at the suitable position and then start the automated measurement.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for measuring a dose distribution of an x-ray beam in a computed tomography apparatus, said x-ray beam being emitted from an x-ray source of said computed tomography apparatus and striking a detector line of a radiation detector of said computed tomography apparatus, said computed tomography apparatus also having a radiation diaphragm disposed in a path of said x-ray beam, said method comprising:

setting a thickness of said x-ray beam in a thickness direction by adjusting said radiation diaphragm to at least one setting;

disposing a slit diaphragm in said path of said x-ray beam preceding said detector line; and detecting a dose distribution of said x-ray beam with said detector line.

2. A method as claimed in claim 1 comprising automatically adjusting said radiation diaphragm through a plurality of settings while acquiring said dose distribution.

3. A method as claimed in claim 2 wherein said radiation diaphragm comprises a diaphragm element with a plurality of apertures therein having respectively different widths, and wherein the step of automatically adjusting said radiation diaphragm comprises automatically displacing said diaphragm element to successively bring said apertures into said path of said x-ray beam.

4. A method as claimed in claim 3 wherein the step of automatically displacing said diaphragm element comprises displacing said diaphragm element with a stepper motor.

5. A method as claimed in claim 4 comprising, from said stepper motor, identifying a position of said diaphragm element for correlation with said acquisition of said dose distribution.

6. A method as claimed in claim 3 wherein the step of displacing said radiation element comprises displacing said radiation element with a constant speed during acquisition of said thickness distribution.

7. A method as claimed in claim 1 wherein said radiation diaphragm comprises two diaphragm plates movable relative to each other to adjust a width of an aperture disposed in said path of said x-ray beam defined by a spacing between said two diaphragm plates, and wherein the step of adjusting said radiation diaphragm comprises automatically moving said two diaphragm plates relative to each other through a plurality of different widths of said aperture.

8. A method as claimed in claim 7 wherein the step of automatically moving said diaphragm plates relative to each other comprises automatically moving said diaphragm plates relative to each other with a stepper motor.

9. A method as claimed in claim 8 comprising, from said stepper motor, identifying respective positions of said two diaphragm plates relative to each other for correlating the respective widths of said aperture with said acquisition of said dose distribution.

10. A method as claimed in claim 1 comprising automatically calculating a half intensity width from said dose distribution.

11. A method as claimed in claim 10 comprising storing said half intensity width.

12. A method as claimed in claim 1 comprising automatically calculating a 10% width from said dose distribution.

13. A method as claimed in claim 12 comprising storing said 10% width.

14. A method as claimed in claim 1 comprising automatically calculating an edge steepness of said dose distribution.

15. A method as claimed in claim 14 comprising storing said edge steepness.

16. A method as claimed in claim 1 wherein said computed tomography apparatus includes a patient table, and wherein the step of disposing a slit diaphragm in front of said detector line comprises mounting said slit diaphragm to said patient table.

17. A method as claimed in claim 1 comprising employing, as said slit diaphragm, a diaphragm having a slit with a width of less than 1 mm.

* * * * *